US009931094B2

United States Patent
Allmendinger et al.

(10) Patent No.: US 9,931,094 B2
(45) Date of Patent: Apr. 3, 2018

(54) METHOD FOR GENERATING X-RAY IMAGE DATA OF AN EXAMINATION OBJECT WITH SUPPRESSED CALCIUM SIGNAL

(71) Applicant: Siemens Healthcare GmbH, Erlangen (DE)

(72) Inventors: Thomas Allmendinger, Forchheim (DE); Steffen Kappler, Effeltrich (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 15/266,382

(22) Filed: Sep. 15, 2016

(65) Prior Publication Data

US 2017/0086769 A1  Mar. 30, 2017

(30) Foreign Application Priority Data

Sep. 30, 2015 (DE) .................. 10 2015 218 928

(51) Int. Cl.
*G06K 9/00* (2006.01)
*A61B 6/00* (2006.01)
*A61B 6/03* (2006.01)

(52) U.S. Cl.
CPC ............ *A61B 6/5258* (2013.01); *A61B 6/032* (2013.01); *A61B 6/42* (2013.01); *A61B 6/465* (2013.01); *A61B 6/481* (2013.01); *A61B 6/482* (2013.01); *A61B 6/503* (2013.01); *A61B 6/504* (2013.01); *A61B 6/5205* (2013.01);
(Continued)

(58) Field of Classification Search
None
See application file for complete search history.

(56) References Cited

U.S. PATENT DOCUMENTS

2005/0163283 A1 7/2005 Bruder et al.
2008/0260092 A1 10/2008 Imai et al.
(Continued)

FOREIGN PATENT DOCUMENTS

DE 102004004295 A1 8/2005
DE 102007053511 A1 5/2008
(Continued)

OTHER PUBLICATIONS

Lehmann L.A., et.al.: "Generalized image combinations in dual KVp digital radiography", in: Med Phys., vol. 8, pp. 659-667; 1981.
(Continued)

*Primary Examiner* — Atiba O Fitzpatrick
(74) *Attorney, Agent, or Firm* — Harness, Dickey & Pierce, P.L.C.

(57) ABSTRACT

A method is for generating X-ray image data of an examination object with reduced calcium blooming. The X-ray image data is based on X-ray projection data acquired with an energy-selective X-ray detector and in respect of at least two energy windows. An embodiment of the method includes determining a calcium content in the X-ray projection data by way of a base material analysis, the calcium content describing the calcium-determined part of the X-ray attenuation caused by the examination object; generating a mixed X-ray projection data record with calcium content suppressed by way of a weighting factor of less than one; and reconstructing the X-ray image data from the mixed projection data record by applying a reconstruction algorithm.

15 Claims, 3 Drawing Sheets

(52) U.S. Cl.
CPC .......... *A61B 6/5217* (2013.01); *A61B 6/4241* (2013.01); *A61B 6/467* (2013.01)

(56) References Cited

U.S. PATENT DOCUMENTS

| | | |
|---|---|---|
| 2010/0014737 A1 | 1/2010 | Ruhrnschopf et al. |
| 2011/0280458 A1 | 11/2011 | Flohr et al. |
| 2012/0207270 A1 | 8/2012 | Flohr et al. |
| 2014/0086383 A1 | 3/2014 | Huwer et al. |

FOREIGN PATENT DOCUMENTS

| | | |
|---|---|---|
| DE | 102008030552 A1 | 12/2009 |
| DE | 102010020770 A1 | 11/2011 |
| DE | 102011004120 A1 | 8/2012 |
| DE | 102012217555 A1 | 3/2014 |

OTHER PUBLICATIONS

Spahn M.: "Flat Detectors and their Clinical Applications", in: Eur Radiol., vol. 15, pp. 1934-1947 ; 2005.
German Office action for application No. 10 2015 218 928.7 dated Feb. 23, 2016.

METHOD FOR GENERATING X-RAY IMAGE DATA OF AN EXAMINATION OBJECT WITH SUPPRESSED CALCIUM SIGNAL

PRIORITY STATEMENT

The present application hereby claims priority under 35 U.S.C. § 119 to German patent application number DE 102015218928.7 filed Sep. 30, 2015, the entire contents of which are hereby incorporated herein by reference.

FIELD

At least one embodiment of the invention generally relates to a method for generating X-ray image data of an examination object in which an X-ray attenuation signal caused by calcium is suppressed, to a corresponding X-ray image data processing device, to a corresponding X-ray system and/or to a corresponding computer program product.

BACKGROUND

When displaying blood vessels of a patient by way of X-ray images, e.g. in the case of CT (computerized tomography) angiography, based on recording with iodine as the contrast medium iodine is administered to the patient just before the start of a scan. At the time of recording, the vessels or lumens to be examined thereby are enriched with the contrast medium. Due to its high atomic number iodine causes a strong X-ray attenuation and therefore provides a clearly visible contrast, so the state of the vessels can be assessed very easily. However, there are often difficulties when displaying the vessel if calcifications occur in the vessel to be examined.

Due to its similarly very high intrinsic contrast, the calcium is shown enlarged and outshines the visible lumen. The calcifications therefore appear much larger in the X-ray image than they actually are. Colloquially this artifact is called the "blooming effect" or "calcium blooming". It is primarily based on the combination of the high intrinsic contrast of the calcium with a relatively soft reconstruction kernel during image generation from the raw data and a windowing of the X-ray image optimized to the iodine contrast and habitual for the observer. In contrast to a hard reconstruction kernel, a soft reconstruction kernel obscures object edges and thereby reduces the resolution but causes less noise in the reconstructed X-ray image. From a clinical perspective it would be desirable to display a calcification as far as possible in its "original size" during the course of reconstruction or during presentation in order to be able to meaningfully medically assess the blood vessel and the extent of its calcification.

One possibility for reducing the blooming in the presentation of calcifications consists in a reconstruction having very sharp reconstruction kernels which depict object edges more sharply in space. This leads to improved mapping of the calcification due to the reconstruction and therewith to a meaningful presentation of the calcification within the iodine windowing. At the same time, however, this method can only be used to a limited extent since the noise in the image increases significantly, and consequently this often can no longer be used for diagnostic purposes.

Alternatively it is known by way of suitable combination of an image with and an image without contrast medium to calculate the signal component caused by the calcium from the X-ray image. Since the calcium blooming occurs in both images, this effect is cancelled out with subtraction and only the lumen remains. However, with this process a further scan is required, and this means additional exposure to radiation for the patient and requires additional computing effort (e.g. registration) to compensate possible, movement-determined deviations in the images due to the temporal offset of the scans.

Furthermore, there are methods for the identification and elimination of the calcium on the basis of dual-energy systems, such as described, for example, in patent application DE 10 2011 004 120 A1. Therein X-ray images of a patient are generated with two different X-ray quantum energies which are then used to identify the X-ray attenuation caused by calcium and iodine and to suppress the attenuation in the images caused by calcium such that more realistic mapping of the of calcifications results. However, this procedure also requires additional exposure to radiation for the patient, because, as a rule, the X-ray images are acquired simultaneously with two X-ray sources (dual source) having different acceleration voltage or via one X-ray source and fast kV switching. Furthermore, owing to its spatial or temporal offset, an evaluation of this X-ray data is limited to observations in the image space.

By contrast, it is the object of the present invention to provide improved measures for generating X-ray image data corrected by the calcium blooming which overcome said drawbacks of the prior art.

SUMMARY at least one embodiment of the invention includes an X-ray image data processing device, an X-ray system and/or a computer program.

The inventive embodiments will be described below in respect of the claimed method as well as in respect of a claimed device. Features, advantages or alternative embodiments mentioned in this connection are similarly to be transferred to the other claimed subject matters and vice versa. In other words, the concrete claims (which are directed, for example, towards a device) can also be developed with the features which are described or claimed in conjunction with a method. The corresponding functional features of the method are formed by appropriate concrete modules or units of the device.

A first embodiment of the invention relates to a method for generating X-ray image data of an examination object, wherein the X-ray image data is calculated from X-ray projection data, wherein the X-ray projection data comprises one first and at least one second X-ray projection data record which has been acquired with an energy-selective X-ray detector and in respect of a specific energy window in each case. The method comprises the following steps:

determining a calcium content in the X-ray projection data by way of a base material analysis, wherein the calcium content describes the calcium-determined part of the X-ray attenuation caused by the examination object, generating a mixed X-ray projection data record with calcium content suppressed by way of a weighting factor of less than one, and reconstructing the X-ray image data from the mixed-projection data record by applying a reconstruction algorithm.

A further embodiment of the present invention relates to a method for generating X-ray image data of an examination object, wherein the X-ray image data is calculated from X-ray projection data, wherein the X-ray projection data comprises one first and at least one second projection data record which has been acquired with an energy-selective X-ray detector and in respect of a specific energy window in each case, comprising the following steps:

reconstructing individual-X-ray image data records for each of the energy windows from the X-ray projection data records using a reconstruction algorithm, and generating a mixed X-ray image data record by weighted addition of the first and the at least one second individual X-ray image data record, wherein weighting factors for the individual X-ray image data records are chosen such that a calcium content in the mixed X-ray image data record is suppressed.

A further embodiment of the invention relates to an X-ray image data processing device for generating X-ray image data of an examination object, which is set up to carry out an embodiment of the inventive method. For this purpose the X-ray image data processing device can, according to a further embodiment of the invention, be designed for generating X-ray image data of an examination object, wherein the X-ray image data is calculated from X-ray projection data, wherein the X-ray projection data comprises one first and at least one second projection data record which has been acquired with an energy-selective X-ray detector and in respect of a specific energy window in each case. For this purpose the X-ray image processing device can comprise a determining unit set up to determine a calcium content in the X-ray projection data by way of a base material analysis, wherein the calcium content describes the calcium-determined part of the X-ray attenuation caused by the examination object, a generating unit set up to generate a mixed X-ray projection data record with calcium content suppressed by way of a weighting factor of less than one, and a reconstruction unit set up to generate X-ray image data from the mixed projection data record by applying a reconstruction algorithm, or a reconstruction unit set up to reconstruct individual X-ray image data records for each of the energy windows from the X-ray projection data records using a reconstruction algorithm, and a generating unit set up to generate a mixed X-ray image data record by weighted addition of the first and at least one second individual X-ray image data record, wherein weighting factors for the individual image data records are chosen such that a calcium content in the mixed image data is suppressed.

A further embodiment of the invention also relates to an X-ray system, comprising an energy-selective X-ray detector set up to acquire one first and at least one second projection data record in respect of a specific energy window in each case, and to an embodiment of the inventive X-ray image data processing device. The X-ray image data processing device is therefore preferably part of an X-ray system having an energy-selective X-ray detector for the acquisition of spectrally resolved X-ray projection data records of an examination object. This means the X-ray image data processing device can be installed, for example, on a control and evaluation computer of the X-ray system. Basically an X-ray image data processing device of this kind can, however, also be implemented in other computer units which are connected, for example, to an X-ray system of this kind via a network for data acquisition, or can be supplied with appropriate image data records in some other way.

A final embodiment of the invention relates to a computer program product which can be loaded directly into a memory of an image data record processing device, having program code fragments to carry out all steps of an embodiment of an inventive method when the program is run in the image data processing device.

BRIEF DESCRIPTION OF THE DRAWINGS

The above-described properties, features and advantages of this invention and the manner in which they are achieved will become clearer and more comprehensible in connection with the following description of the example embodiments which are illustrated in more detail in connection with the drawings. This description does not limit the invention to these example embodiments. In the drawings.

DETAILED DESCRIPTION OF THE EXAMPLE EMBODIMENTS

Figure 1:
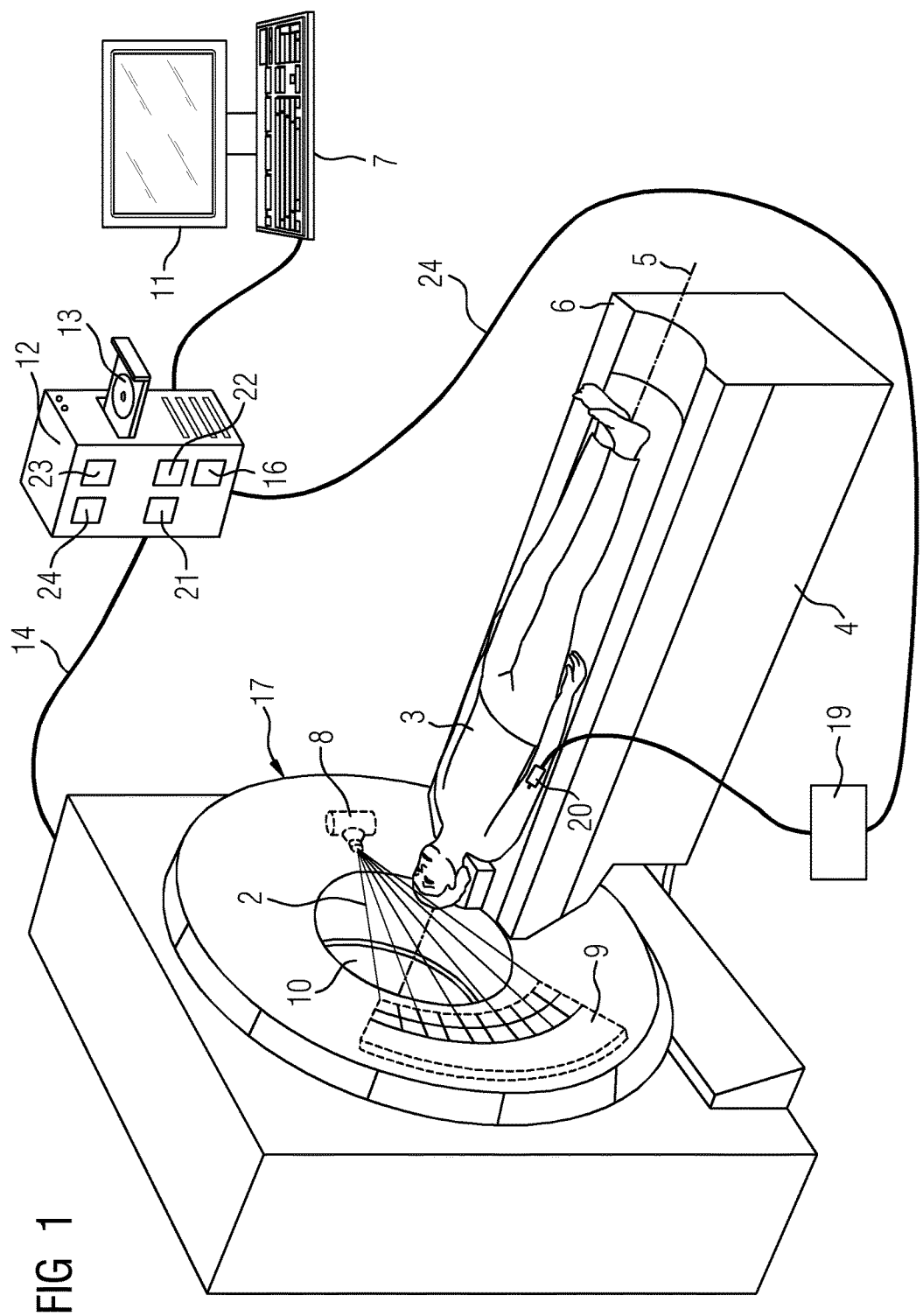
FIG. 1 shows an inventive X-ray system in an example embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

A first embodiment of the invention relates to a method for generating X-ray image data of an examination object, wherein the X-ray image data is calculated from X-ray projection data, wherein the X-ray projection data comprises one first and at least one second X-ray projection data record which has been acquired with an energy-selective X-ray detector and in respect of a specific energy window in each case. The method comprises the following steps:

determining a calcium content in the X-ray projection data by way of a base material analysis, wherein the calcium content describes the calcium-determined part of the X-ray attenuation caused by the examination object, generating a mixed X-ray projection data record with calcium content suppressed by way of a weighting factor of less than one, and reconstructing the X-ray image data from the mixed-projection data record by applying a reconstruction algorithm.

With at least one embodiment of the proposed method, at least two X-ray projection data records relating to different X-ray quantum energy distributions are acquired from the examination object, as a rule a patient with a medical issue. These records provide spectrally resolved information about the X-ray attenuation due to the examination object. The X-ray projection data records can be acquired with at least one embodiment of an inventive X-ray system which is described in more detail below. The use of an energy-selective X-ray detector enables simultaneous acquisition of the X-ray projection data records, and this enables evaluation of the X-ray projection data in the projection space, i.e. before an image reconstruction. On the other hand, the inventive process does not require an additional X-ray examination in the case of projection data recording, so the overall dose can advantageously be kept low for the examination object.

Two or more energy windows can be detected at the same time. The number of energy windows that are actually scanned results, for example, from the design of the X-ray detector, and the medical issue.

The X-ray projection data records can relate to a section of the body of the examination object, for example a specific body region of the patient, e.g. a specific region of the heart, which is to be mapped via X-ray system. In this case the X-ray projection data records contain information about the X-ray attenuation distribution of the examination object only in respect of the section to be mapped. The X-ray projection data records alternatively relate to the entire body of the examination object. In this case the image data records contain information about the X-ray attenuation distribution of the examination object in respect of the entire body.

The X-ray image data represent one or more X-ray images, in particular a temporal sequence of X-ray images of one and the same body region of the examination object.

The base material analysis is a method known among experts for identifying a content in a scanned X-ray attenuation signal which can be attributed to a known base material. The base material analysis can firstly be based on X-ray image data and secondly on X-ray projection data or raw data. It can also be carried out in the image space as well as in the projection space. The raw data-based base material analysis is described in more detail, for example, in Med Phys. 1981 September-October; 8(5):659-67 "Generalized image combinations in dual KVP digital Radiography", the entire contents of which are hereby incorporated herein by reference. At least one embodiment of the inventive method is capable of carrying out an evaluation according to base materials directly in the projection space even before image reconstruction.

With raw data-based base material analysis, the energy-resolved X-ray projection data can be described for each projection direction as a linear combination of products of thickness, density and the quotients of X-ray attenuation coefficient and density of a base material in each case which, due to the presence of a plurality of scanning signals for different energy windows respectively, can be resolved according to the product of material density and material thickness. According to at least one embodiment of the invention calcium is chosen as one of the base materials which is primarily responsible for the X-ray attenuation due to calcifications in blood vessels.

The X-ray attenuation signal content, within an X-ray projection, which can be attributed to calcium, can be identified in this way. In a next step of the inventive method X-ray projection data is generated in the form of a mixed X-ray projection data record, which data is distinguished in that the calcium-determined signal component is suppressed. The mixed X-ray projection data record comprises the X-ray projection data of all projection directions acquired during the energy-selective scan, wherein mixing the calcium signal component with signal components of at least one other material or tissue occurs within only one projection direction in each case.

X-ray projection data follows from this, in which the calcium signal is attenuated. For this purpose a weighting factor of less than one is determined for the calcium content. In other words, the calcium-determined signal component is attenuated with respect to other signal components of the acquired X-ray attenuation signal. In a next step X-ray image data is reconstructed from the X-ray projection data generated in this way. This data has a reduced calcium contrast due to the inventive manipulation of the spectrally resolved X-ray projection data records. This is expressed in a realistic illustration or presentation of the sizes or dimensions of calcifications in the mapped body region of the examination object, so vessel calcifications and/or the state of the surrounding vessels can be medically assessed using the X-ray image data. Blooming can be advantageously reduced or suppressed in this way.

A reconstruction or a reconstruction algorithm within the meaning of this invention is any image reconstruction algorithm known among experts, for example a weighted, filtered back projection (WFBP), as is frequently used, for example, in computerized tomography. Alternative reconstruction algorithms are also possible and their application falls within an expert's field of competence.

In an advantageous development of at least one embodiment of the invention the weighting factor for the calcium content is between 0.25 and 0.75. The inventors have recognized that a weighting factor within said limits delivers the best results in respect of the visual impression to be achieved for the X-ray image data. It is particularly advantageous if the X-ray system has stored a value for the weighting factor within said value range as a default value, for example in a memory provided for this purpose, which value is, as a rule, automatically used when generating X-ray image data if there are no other inputs or criteria. In one example embodiment the value for the weighting factor is adjusted to the X-ray system used for acquiring the X-ray projection data, or to individual components of the system, such as X-ray detector, X-ray source, the recording mode, the X-ray protocol or the underlying medical issue. In a further example embodiment the weighting factor is based on purely empirical observations or empirical values of a user.

In a preferred embodiment of the invention the weighting factor for the calcium content can be specified and/or adjusted by a user. This can be provided as an alternative to or in addition to a default value for the weighting factor pre-set by the X-ray system.

According to a further embodiment of the invention it is particularly advantageous if the weighting factor for the calcium content is determined according to a desired visual impression of the reconstructed image data. For this purpose it can be provided that an X-ray image adjusted by the blooming by way of default value, or value for the weighting factor input for the first time by the user, is firstly displayed for a user and the user can decide with the aid of the image impression whether a different value would be more suitable for the weighting factor. An optimum image impression, because it matches the desired one, can be attained by way of an appropriate iterative process in which the user can input multiple values for the weighting factor and he can immediately be provided with a display of a corresponding X-ray image. Alternatively, it can be provided that X-ray images having different calcium weightings are simultaneously displayed for a user, so he can derive at a glance an X-ray image that corresponds to a desired image impression, or derive valuable medical information from the comparison of individual images among themselves.

In a further development of at least one embodiment of the invention base material analysis and generation of the mixed projection data record are carried out before filter kernel convolution of the reconstruction algorithm. In this connection the inventors have recognized that, apart from reducing the spatial resolution, filter kernel convolution of the reconstruction and the increase in noise continues to have an adverse effect on the X-ray projection data. Convolution therefore sometimes causes overshoots or undershoots in the X-ray projection data which can contribute to falsification of the image information and therefore cause inaccuracies in the mapping of the real conditions in the examination object. In order not to amplify these effects as a result of the weighting of the calcium content, base material analysis and mixed X-ray projection data generation ideally occur using the raw data or X-ray projection data records that have not yet been manipulated.

According to a further embodiment of the inventive method, in addition to calcium the base material analysis is carried out in respect of at least one of the following materials: iodine and human soft tissue. Other materials are likewise possible. "Material" can be taken to mean any desired substance or any desired tissue or any tissue type or any desired combination thereof. If the mixed X-ray projection data record in any projection direction is composed of a linear combination of the calcium signal and the signal component of at least one of other materials, a particularly good adjustment of the calcium contrast can be achieved by selecting a suitable weighting factor. In one variant the signal component of the at least one further material is weighted with one. In a further variant this signal component can also be provided with a weighting factor corresponding to an optimum, because it is desired, image impression, and this can be specified and/or adjusted automatically or by a user.

A further embodiment of the present invention relates to a method for generating X-ray image data of an examination object, wherein the X-ray image data is calculated from X-ray projection data, wherein the X-ray projection data comprises one first and at least one second projection data record which has been acquired with an energy-selective X-ray detector and in respect of a specific energy window in each case, comprising the following steps:

reconstructing individual-X-ray image data records for each of the energy windows from the X-ray projection data records using a reconstruction algorithm, and generating a mixed X-ray image data record by weighted addition of the first and the at least one second individual X-ray image data record, wherein weighting factors for the individual X-ray image data records are chosen such that a calcium content in the mixed X-ray image data record is suppressed.

This embodiment of the invention is also based on acquisition of X-ray projection data by way of an energy-selective detector, in other words, spectrally resolved information about the X-ray attenuation properties of an examination object, generally also a patient here, is acquired at the same time, i.e. within one scan, according to this aspect as well. The inventors have recognized that this spectral information can also be utilized in another way in order to achieve improved image quality in respect of reduced calcium blooming. In contrast to the first aspect of the invention, here individual X-ray image data records are first of all generated from the X-ray projection data records. A known reconstruction algorithm can likewise be used for this purpose, e.g. a weighted, filtered back projection or the like. In other words, spectrally resolved X-ray image data records are generated here. These are then combined to form a mixed X-ray image data record which corresponds to the X-ray image data, wherein individual image data records are each weighted such that a calcium content is in turn suppressed in the mixed X-ray image data. This process likewise advantageously enables material-selective attenuation or weighting of signal components without an examination object having to be burdened with an additional dose for this purpose. The X-ray image data can correspond, for example, to one or a series of X-ray image(s) in this case as well.

In contrast to the embodiment mentioned first, the spectrally resolved image information is manipulated in the image space and not in the projection space in order to increase the quality.

In a development of this embodiment of the invention, the weighted addition of the at least two individual X-ray image data records occurs image element for image element. In the case of two-dimensional image data an image element is taken to mean a pixel; in the case of three-dimensional image data it is taken to mean a voxel. The inventively reconstructed individual X-ray image data records each have image elements corresponding to one and the same position in the space. According to this development, weighting and addition occur in respect of the image contents of these corresponding image elements. In other words, the brightness values of the corresponding image elements are added in a weighted manner in each case, and, more precisely, image element for image element.

In a further embodiment of the invention, the respective weighting factors are individually ascertained for each image element that corresponds in the individual X-ray image data sets. In other words, the weighting factors for individual image elements differ from each other within an X-ray image data record. In this way the image quality of the mixed X-ray image data record can be further improved by particularly exact attention to local conditions and contrasts.

In a particularly preferred embodiment of the invention according to the second embodiment, the weighting factors result as a function of the ratio of the CT number (Hounsfield number) in a respective image element of the first and the at least one second individual X-ray image data record. In other words, the image contents, intensity or brightness or the like are used on the respective image elements to derive a suitable weighting for the individual image contents. This process takes into account the fact that calcium blooming is present in all spectrally resolved X-ray image data sets and the image element contents are also corrected by an involved calcium signal at whose position in the space there is no calcium at all. Calcium blooming is therefore universally corrected in the X-ray image data records.

According to a further embodiment of the invention, according to the second embodiment, the weighting factors ascertained for the mixed X-ray image data record are standardized. As a result an image impression that is familiar to the observer can be retained overall. In other words, the remaining weighting factor(s) necessary for generating the mixed X-ray image data record follow(s) from the weighting factor ascertained for one of the individual image data records.

In a development of the invention according to the first or second embodiment, the first projection data record is acquired in respect of the energy window 25-65 keV and the at least one second projection data record is acquired in respect of the energy window 65-140 keV. The first projection data record therefore corresponds to a low-energy data record and the at least one second projection data record to a high-energy data record. Alternative energy windows are likewise possible. Furthermore, more than two energy windows can be resolved by the energy-selective X-ray detector, wherein the energy windows ideally do not then intersect.

In a further embodiment of the invention according to the first or the second embodiment, the at least one weighting factor is determined empirically, experimentally with the aid of X-ray image data which has been acquired with the same or a comparable X-ray system and/or via a simulation of the X-ray system. This embodiment takes into account the recognition that weighting factors are dependent not only on energy combination but also on the X-ray system or type of X-ray system with which the X-ray projection data is acquired.

In a preferred variant a system- or device-specific weighting factor of this kind can be determined experimentally with the aid of image data which is based on scan data which has been acquired with the same X-ray system or the same type of X-ray system. Additionally or alternatively, suitable simulations of such scans can also be carried out with an appropriate X-ray system or type of X-ray system and be used to ascertain the weighting factor(s).

A further embodiment of the invention relates to an X-ray image data processing device for generating X-ray image data of an examination object, which is set up to carry out an embodiment of the inventive method. For this purpose the X-ray image data processing device can, according to a further embodiment of the invention, be designed for generating X-ray image data of an examination object, wherein the X-ray image data is calculated from X-ray projection data, wherein the X-ray projection data comprises one first and at least one second projection data record which has been acquired with an energy-selective X-ray detector and in respect of a specific energy window in each case. For this purpose the X-ray image processing device can comprise a determining unit set up to determine a calcium content in the X-ray projection data by way of a base material analysis, wherein the calcium content describes the calcium-determined part of the X-ray attenuation caused by the examination object, a generating unit set up to generate a mixed X-ray projection data record with calcium content suppressed by way of a weighting factor of less than one, and a reconstruction unit set up to generate X-ray image data from the mixed projection data record by applying a reconstruction algorithm, or a reconstruction unit set up to reconstruct individual X-ray image data records for each of the energy windows from the X-ray projection data records using a reconstruction algorithm, and a generating unit set up to generate a mixed X-ray image data record by weighted addition of the first and at least one second individual X-ray image data record, wherein weighting factors for the individual image data records are chosen such that a calcium content in the mixed image data is suppressed.

An inventive X-ray image data processing device of an embodiment can be used for carrying out the inventive method. This advantageously comprises an X-ray image data interface or an X-ray projection data interface in order to adopt the corresponding data records. It can also comprise an interface for adopting at least one weighting factor, for example on the basis of inputs of a user or from a memory in which weighting factors are stored.

The various units, such as reconstruction or generating units, of the X-ray image data processing device can be implemented on a suitable computer as software modules. The data interface and the interface for adopting the weighting factor can likewise be implemented in the form of pure software if only one adoption of the data records or the weighting factor from other pre-processing devices implemented, for example, on the same computer unit, or from storage devices is required.

Basically these interfaces can also be implemented as combined hardware-/software interfaces, however, in order to achieve external adoption, for example with the aid of software components of specially configured hardware interfaces. The X-ray image data processing device conventionally also has an output interface for outputting the generated X-ray image data, for example into a suitable memory and/or directly to a user on a screen or a printer. This output interface can also be pure software or a combined hardware/software interface.

A largely software-based implementation has the advantage that existing X-ray image data processing devices can be easily upgraded by way of a software update in order to work inventively.

A further embodiment of the invention also relates to an X-ray system, comprising an energy-selective X-ray detector set up to acquire one first and at least one second projection data record in respect of a specific energy window in each case, and to an embodiment of the inventive X-ray image data processing device. The X-ray image data processing device is therefore preferably part of an X-ray system having an energy-selective X-ray detector for the acquisition of spectrally resolved X-ray projection data records of an examination object. This means the X-ray image data processing device can be installed, for example, on a control and evaluation computer of the X-ray system. Basically an X-ray image data processing device of this kind can, however, also be implemented in other computer units which are connected, for example, to an X-ray system of this kind via a network for data acquisition, or can be supplied with appropriate image data records in some other way.

In an embodiment, the X-ray system is an X-ray device which is designed for recording a single X-ray projection or a large number of X-ray projections from the same or different projection angles or projection directions. In a further embodiment of the invention the X-ray system can be designed, for example, as a computer tomograph, angiography system, projection radiography system or the like.

In particular, the X-ray system is a computer tomograph having an annular rotating frame, or a C-arm X-ray device which can be used for both types of image recording. The X-ray images can be generated, for example, during a, in particular continuous, rotational movement of a recording unit comprising an X-ray radiation source and an X-ray detector that cooperates with the X-ray radiation source.

Alternatively a plurality of X-ray images are acquired in one projection direction, during which time the cooperating X-ray radiation source and X-ray detector are not moved. An X-ray detector for a computer tomograph is, for example, a line detector having a plurality of lines. An X-ray detector for a C-arm X-ray device is, for example, a flat panel detector. Within the context of the invention the X-ray detector can be designed so as to be both integrating and counting. In any case it is an energy-sensitive or energy-selective X-ray detector. This facilitates or enables the simultaneous acquisition of X-ray image data while at the same time offering flexible further processing options.

Energy-integrating X-ray detectors are currently primarily based on scintillators, for example made from CsJ or Gd2O2S, which, for example, convert X-ray radiation in to comparatively low-energy radiation, for example visible light. This light is converted into matrices of photodiodes in electrical charge. These are then conventionally read line-by-line by active control elements. The principle construction encompassed by what are referred to as indirect conversion X-ray detectors has a scintillator, an active read-out matrix made from amorphous silicon or designed in CMOS technology with a large number of pixel elements (with photodiode and switching element) and electronic control and read-out devices (see for example M. Spahn, "Flat detectors and their clinical applications", Eur Radiol. (2005), 15: 1934-1947), the entire contents of which are hereby incorporated herein by reference. Integrating X-ray detectors do not discriminate the incident radiation according to its quantum energy.

Energy-sensitive or -selective should be taken to mean spectrally resolving or spectrally separating. Energy-selective detectors are set up to categorize incident radiation quanta according to their quantum energy. These detectors have the advantage that they are suitable for simultaneously generating at least two X-ray data records which differ in their quantum energy distribution. Energy-selective detectors are, for example, quantum counting detectors or integrating two-layer detectors.

A quantum counting detector is typically a direct conversion detector which converts an incident radiation quantum directly into an electrical signal by way of suitable detector material. Quantum counting detectors can be operated in an energy-resolving manner, wherein the energy resolution can be adjusted by way of what is known as binning. In other words, almost any energy ranges can be specified in respect of which incident X-ray quanta can be categorized.

The at least two X-ray data records are each formed by signals within one or more energy range(s). In particular, the semi-conductors cadmium telluride, cadmium zinc telluride or gallium arsenide or, in the case of a flat-panel detector, amorphous selenium or the like are suitable as detector materials for quantum counting detectors in medical computerized tomography. Quantum counting, energy-selective X-ray detectors are not limited in terms of their applicability to the invention. Two or even more energy bins or energy windows can be considered at the same time and then be evaluated.

A two-layer detector or dual- or double-layer detector is designed to segment the incident radiation spectrum into low-energy and high-energy portions. For this purpose the two-layer detector is composed of two layers. A detector layer facing the X-ray radiation source measures radiation quanta of the incident radiation with a low energy and allocates the measured signals to the first X-ray data record. The layer is penetrated by high-energy radiation. Photons with relatively high quantum energy are measured in the detector layer arranged below or behind, i.e. remote from the X-ray radiation source, and are allocated to the second X-ray data record.

Both detector layers typically comprise a scintillator; the two-layer detector is consequently an indirect conversion detector. Crystals such as a cesium iodide, cadmium tungstate or ceramic materials, such as, for example, gadolinium oxysulfide or the like are used as scintillation material. Two-layer detectors are then particularly suitable for the present invention if one of the energy thresholds between high-energy and low-energy radiation is close to or above the focus of the energy spectrum or the rapidly increasing range of the absorption coefficient of the filter.

A final embodiment of the invention relates to a computer program product which can be loaded directly into a memory of an image data record processing device, having program code fragments to carry out all steps of an embodiment of an inventive method when the program is run in the image data processing device.

The X-ray system 1 shown in FIG. 1 corresponds to an X-ray computer tomograph. The computer tomograph shown here has a recording unit 17, comprising a radiation source 8 in the form of an X-ray source and a radiation detector in the form of an X-ray detector 9. During the recording of X-ray projections the recording unit 17 rotates about a system axis 5, and during the recording the X-ray source emits rays 2 in the form of X-rays. The X-ray source is an X-ray tube. The X-ray detector 9 is a line detector having a plurality of lines. The X-ray detector 9 is, moreover, designed as a quantum counting, energy-selective X-ray detector 9, i.e. it is set up to generate per detector element a plurality of, i.e. at least two, scan data records, which differ in respect of the X-ray quantum energies taken into account in each case.

During the recording of projections a patient 3 lies on an examination table 6. The examination table 6 is therefore connected to a table base 4 such that the base supports the examination table 6 with the patient 3. The examination table 6 is designed to move the patient 3 in a recording direction through the opening 10 in the recording unit 17. As a rule, the recording device is given by the system axis 5 about which the recording unit 17 rotates during recording of X-ray projections. With a spiral scan the examination table 6 is moved continuously through the opening 10 while the recording unit 17 rotates around the patient 3 and records the projection data. The X-rays therefore describe a spiral on the surface of the patient 3.

The X-ray system also comprises a contrast medium administering unit 19. A contrast medium, for example in the form of a solution containing iodine, can be administered to the patient 3 via an injection needle 20 during projection recording. The flow rate of the contrast medium can be controlled by the contrast medium administering unit 19 as a function of time according to a defined injection protocol. The contrast medium administering unit 19 can be integrally designed with the X-ray system or be immovably or movably arranged in the examination room.

The X-ray system has an X-ray image processing device 12 in the form of a computer, which is connected to a display unit 11, for example for graphically displaying reconstructed and corrected X-ray images or for displaying selection menus in respect of a weighting factor for a calcium signal component, and to an input unit 7. The display unit 11 can be, for example, an LCD, a plasma or an OLED screen. It can also be a touch-sensitive screen which is also designed as an input unit 7. Such a touch-sensitive screen can be integrated in the imaging device or be designed as part of a mobile device. The input unit 7 is, for example, a keyboard, mouse, what is known as a "touch-screen" or a microphone for speech input. The input unit 7 can also be set up to recognize movements of a user and convert them into corresponding commands. For example, a weighting factor for a calcium content can be selected by a user via input unit 7.

The X-ray image processing device 12 is connected to the rotatable recording unit 17 in order to exchange data. Firstly control signals for the X-ray image recording are transmitted from the X-ray image processing device 12 to the recording unit 17 by way of an interface unit 21 and connection 14. Different scan protocols each matched to one type of examination can be stored in a memory 24 for this purpose and be chosen by the user before projection data recording. The recording unit 17 is controlled according to the chosen scan protocol. Secondly, recorded projection data, for example in the form of the at least two X-ray projection data records, is acquired in respect of different energy windows for further processing, for example in a further determining unit 16 described in more detail below, by the interface unit 21. The connection 14 is wired or wireless in a known manner. The X-ray image processing device 12 is also connected to the contrast medium administering unit 19 for the exchange of control signals, in particular for the synchronization of contrast medium administration with X-ray image recording. The likewise known wireless or wired connection 14 is available for this purpose.

The X-ray image processing device 12 comprises a reconstruction unit 23 which is set up to generate X-ray image data from the mixed X-ray projection data record or individual X-ray image data records from the at least two spectrally resolved X-ray projection data records according to known reconstruction methods. There is a data connection between display unit 11 and reconstruction unit 23, for example for transmitting and displaying X-ray image data.

The determining unit 16 of the computer system 12 is configured as a projection data processing unit. It is set up to carry out computing steps related to the inventive method on the X-ray projection data records. In particular, the determining unit 16 is designed to carry out a raw data-based material analysis using the at least two X-ray projection data records.

The memory 24 of the X-ray image processing device 12 is designed to store a large number of weighting factors for a calcium content of the X-ray attenuation signal, for example as a function of a specific type of examination, the scan protocol, from experience or based on simulations for retrieval by a generating unit 22. The generating unit 22 is designed to automatically ascertain a suitable weighting factor from the stored weighting factors and use it, for example, as a default value or suggest it to the user. Generating unit 22 and memory 24 are appropriately connected for the exchange of data. Alternatively the X-ray image processing device 12 is connected to an RIS network (RIS=Radiological Information System) or a PACS network (PACS=Picture Archiving and Communication System) for the retrieval of weighting factors which are stored in this case in a RIS or PACS network. The generating unit then generates mixed X-ray projection data with a suppressed calcium signal component using the automatically selected weighting factor or the weighting factor specified by a user. On the other hand, the generating unit 22 is designed to ascertain weighting factors for individual X-ray image data records and, in particular, for individual image elements of the individual X-ray image data records based on the CT numbers or brightness values.

Determining unit 16 and output unit 11 or input unit 7 likewise have a data connection, in order, for example, to be able to show the user a selection menu in respect of the desired base materials available or to be able to receive related information from the user.

In the present case the reconstruction unit 23, determining unit 16 and generating unit 22 are designed as separate modules which, where required, can exchange data with each other. Alternatively all of said units can, for example, also be integrated, be that in the form of a physical or functional integrity.

The X-ray image processing device 12 in the form of the computer system can cooperate with a computer-readable data carrier 13, in particular in order to carry out an inventive method by way of a computer program with program code. The computer program can also be retrievably stored on the machine-readable carrier. In particular, the machine-readable carrier can be a CD, DVD, Blu-ray disc, a memory stick or a hard disk. The reconstruction unit 23, determining unit 16 and generating unit 22 can be designed in the form of hardware or in the form of software. For example, the determining unit 16 is designed as what is referred to as an FPGA (acronym for "Field Programmable Gate Array") or comprises an arithmetic logic unit.

In the example shown here at least one computer program is stored on the memory 24 of the X-ray image processing device 12, and this carries out all method steps of an embodiment of the inventive method when the computer program is run on the computer. The computer program for carrying out the method steps of an embodiment of the inventive method comprises program code. Furthermore, the computer program can be designed as executable files and/or be stored on a different computing system to the computer system 12. For example, the X-ray system can be designed such that the X-ray image processing device 12 loads the computer program for carrying out an embodiment of the inventive method into its internal main memory via an Intranet or via the Internet.

Figure 2:
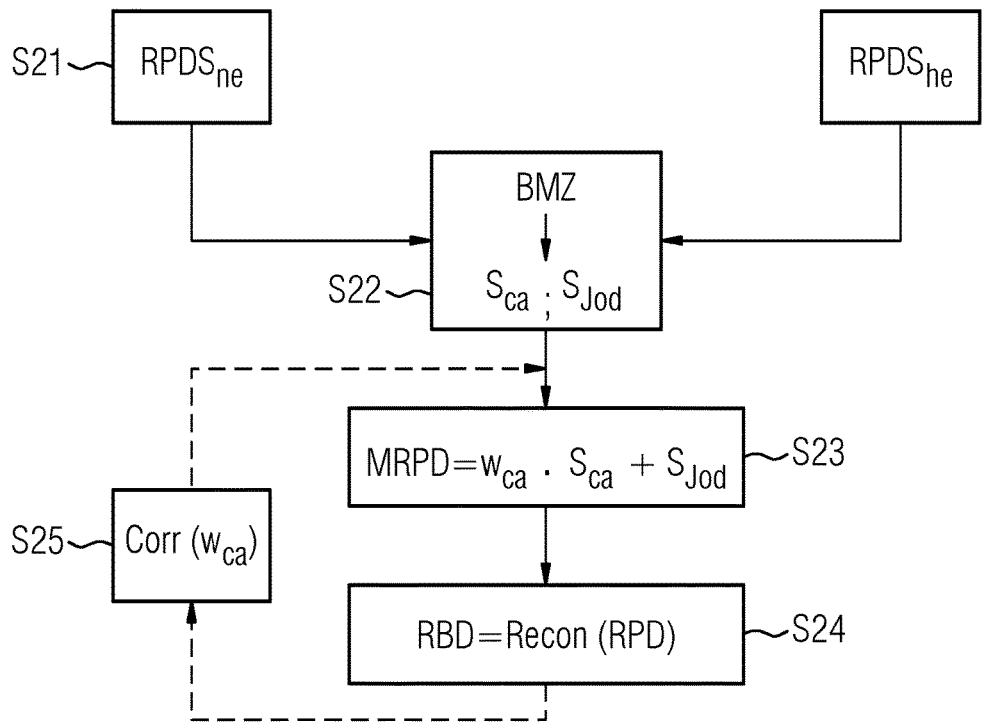
FIG. 2 shows a flow diagram of an inventive method according to one aspect in an example embodiment of the invention.

FIG. 2 shows a flow diagram of an embodiment of the inventive method according to a first aspect in an example embodiment. In a step S21 firstly two X-ray projection data records RPDSne and RPDShe, one relating to a low X-ray quantum energy (ne) and one in respect of a higher X-ray quantum energy (he), of an examination object are simultaneously acquired by administering the contrast medium iodine via energy-sensitive X-ray detector 9 of an X-ray system. These data records RPDSne, RPDShe comprise information in respect of the X-ray quantum energy-dependent X-ray attenuation by the examined body part. The data records RPDSne, RPDShe also comprise X-ray projections in a large number of projection directions. The data records RPDSne, RPDShe are subjected in a second step S22 to a raw data-based material analysis BMZ.

The scanned line integral according to the product of density and material thickness are resolved for the base material calcium and the base material iodine for each projection direction, which are identical in both data records RPDSne and RPDShe, and in each detector element. Therefore the X-ray attenuation content Sca and $S_{Jod}$ of the acquired X-ray signal, which can be attributed to calcium and iodine respectively, is known for each projection direction and for each individual detector element.

In a further step S23 a mixed X-ray projection data record MRPD is generated which is composed of the calcium signal $S_{ca}$ weighted by way of default and the iodine signal $S_{Jod}$ (weighted with one) using a default value for a weighting factor $w_{ca}$ for the signal component $S_{ca}$, here, for example, $w_{ca}$=0.5, which can be attributed to calcium. The default value can be based on purely empirical observations and be stored in a memory of the X-ray system for retrieval.

In step S24 the mixed X-ray projection data record MRPD is subjected to an image reconstruction Recon, for example a weighted, filtered back projection sufficiently known among experts, from which X-ray image data RBD results which can be shown immediately to the user. This is characterized by an improved image quality in respect of the blooming artifact. This artifact is reduced or even eliminated due to the suppressed calcium signal in each individual projection direction, so calcifications, in particular in blood vessels, are displayed in the X-ray image according to their actual size. A clear improvement in the informative value of X-ray images, in particular in angiography, specifically in card-angiography, can therefore be achieved.

In an optional step S25 (broken lines) which can be repeated as often as desired the user can assess the displayed X-ray image and vary the default value for the weighting factor $w_{ca}$ for the calcium content or subject it to a correction Corr until the image impression achieved thereby matches the desired image impression.

Figure 3:
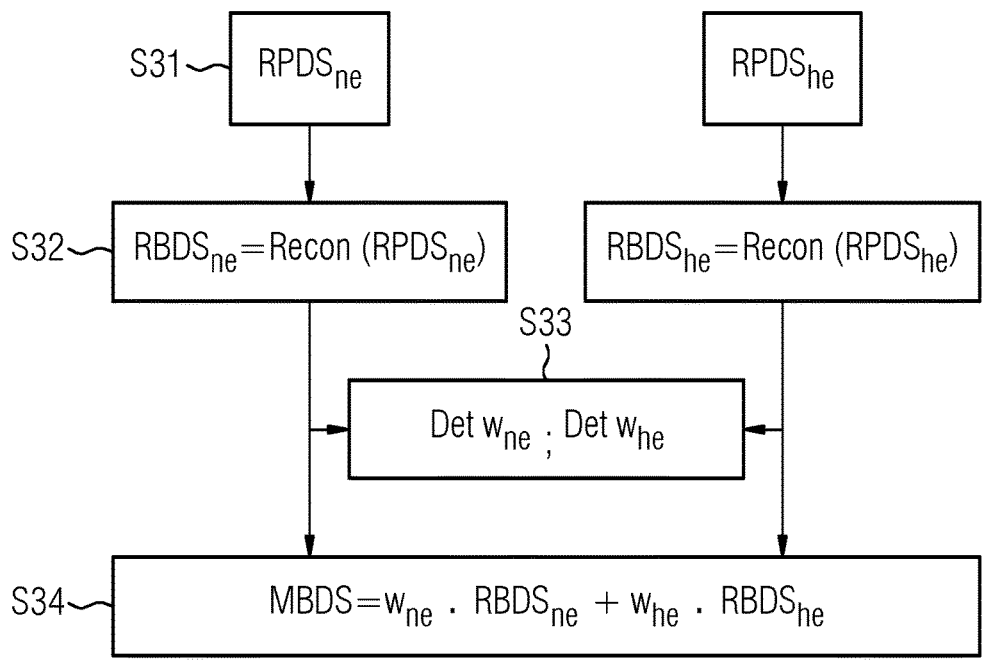
FIG. 3 shows a flow diagram of an inventive method according to a further aspect in a further example embodiment of the invention.

FIG. 3 shows a flow diagram of an embodiment of the inventive method according to a second aspect in a further example embodiment. In contrast to the example embodiment described in FIG. 2, here the calcium signal is suppressed in the image space and not in the projection space.

In a first step S31 firstly two X-ray projection data records RPDSne and RPDShe, one relating to a low X-ray quantum energy (ne) and one in respect of a higher X-ray quantum energy (he), of an examination object are acquired simultaneously via energy-sensitive X-ray detector 9 of an X-ray system by administering the contrast medium iodine. These data records RPDSne, RPDShe comprise information in respect of the X-ray quantum energy-dependent X-ray attenuation by the examined body part. The data records RPDSne, RPDShe also comprise X-ray projections in a large number of projection directions.

In a second step S32 the data records RPDSne, RPDShe are each individually subjected to an image reconstruction, for example a weighted, filtered back projection Recon, resulting in the individual X-ray image data records RBDSne, RBDShe respectively. The reconstruction does not differ from the reconstruction described in relation to FIG. 2, which was applied to the mixed X-ray projection data record MRPD. Other reconstruction methods are of course also conceivable.

Figure 4:
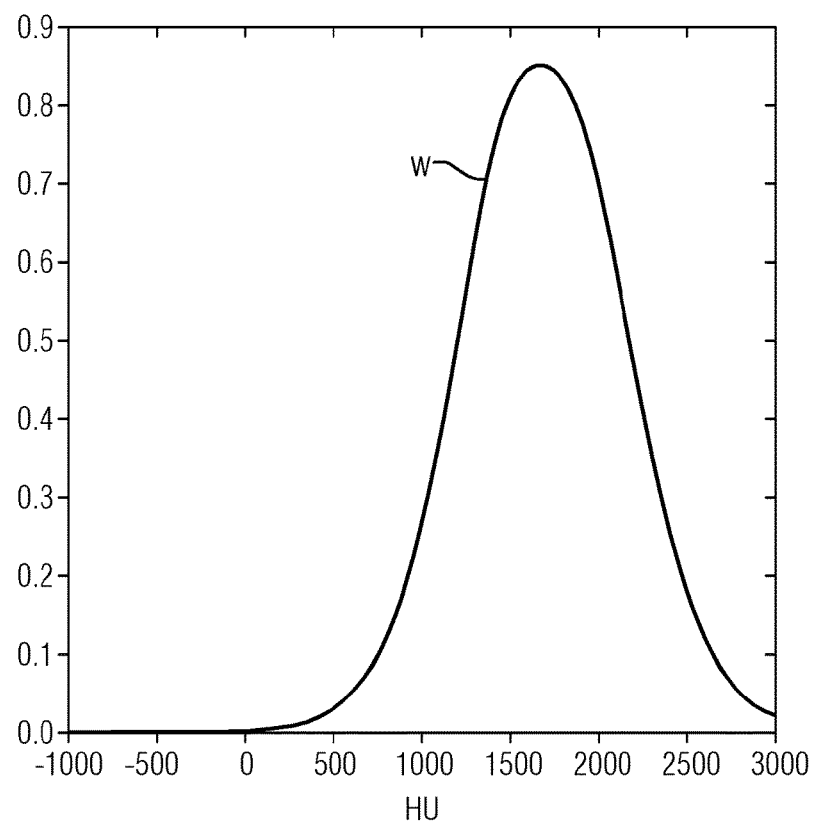
FIG. 4 shows a weighting function as a function of the Hounsfield value according to an example embodiment of the invention.

In a third step S33 weighting factors wne and whe are automatically ascertained for the individual X-ray image data records by way of a determining function Det, and these are chosen such that with a weighted combination of the individual X-ray image data records the calcium content is suppressed in order to reduce the calcium blooming. For this purpose, an embodiment of the invention according to this example embodiment provides that the weighting factor wne for the low-energy X-ray image data record RBDSne is determined individually, according to the weighting function w shown in FIG. 4, for each individual image element as a function of the Hounsfield value (CT number) in the respective image element. The weighting factor whe for the corresponding image element of the high-energy X-ray image data record RBDShe results, by contrast, in accordance with whe=1−wne. In other words, image elements of the low-energy X-ray image data record RBDSne are provided with Hounsfield numbers in the range between 1,200 and 2,200 in this example embodiment, having a weighting factor wne greater than 0.5, wherein the maximum lies at a Hounsfield number of approx. 1,600. Image elements with Hounsfield numbers less than 1,200 and greater than 2,200 are weighted with weighting factors wne less than 0.5. This accordingly results in the values for the weighting factors whe for the corresponding image elements of the high-energy X-ray image data record RBDShe according to the formula given above.

This process with the weighting means that image elements that appear particularly light in the low-energy X-ray image data record are weighted strongly but their pendant of the high-energy image data record is weighted only weakly. This process provides particularly advantageous elimination of calcium blooming. In a final step S34 X-ray image data in the form of a mixed image data record MBDS is generated by image element-wise addition of the individual image data records RBDSne, RBDShe weighted according to the ascertained weighting factors wne, whe, and this can be displayed for a user immediately.

Figure 5:
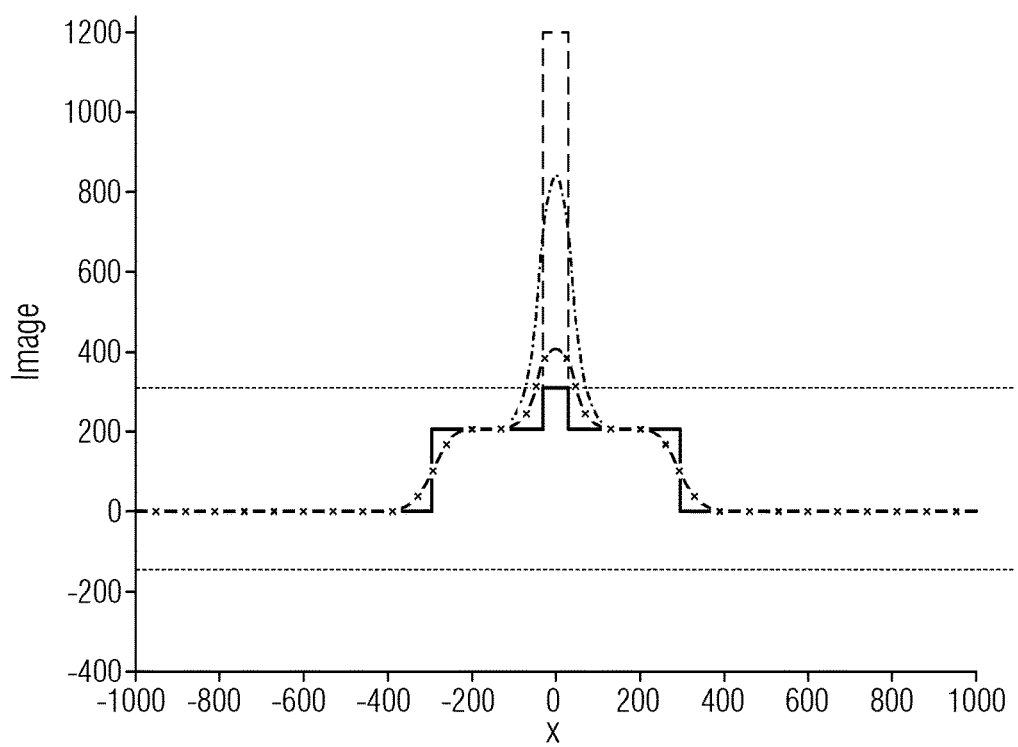
FIG. 5 shows an overview graph to illustrate at least one embodiment of the invention.

An embodiment of the present invention will be summarized again with reference to FIG. 5: a physical structure (lengthways broken-line curve), for example a calcium plaque inside a blood vessel, has a very narrow or limited spatial distribution which for the sake of simplicity extends symmetrically in the space (x) around the zero point from about −300 to +300 along the abscissa of the coordinate system, wherein the signal (approx. between −10 and +10 of the abscissa) caused by the calcium plaque has a signal intensity that is approx. six times stronger than the blood vessel. This results in the simplified stepped signal characteristic of the physical structure. Within the context of conventional X-ray imaging with a known reconstruction algorithm, for example in the case of computerized tomography, the physical structure is mapped with clear differences from the original (dot-dash curve), and this is primarily due to the reconstruction algorithm for the X-ray imaging.

The X-ray image is characterized in particular by an enlargement or expansion of the calcium plaque which extends in the X-ray image from approx. −90 to +90 along the abscissa, as well as of the blood vessel which extends in the X-ray image from approx. −400 to +400 along the abscissa. While the signal of the calcium plaque is primarily based on the X-ray absorption due to calcium, the signal of the blood vessel is based on X-ray absorption by iodine contrast medium in the vessel. To be able to clearly map soft tissue, including the blood vessel, windowing occurs for iodine-typical Hounsfield values between approx. −150 to +300 (short broken lines). In other words, the available gray scales are distributed among said Hounsfield values.

The consequence of this windowing is that almost the entire signal caused by calcium is mapped in the lightest gray scale since its Hounsfield values are for the most part above +300. This leads to said enlargement or blooming of the calcium in the X-ray image. An embodiment of the inventive suppression of the calcium-determined signal content does not prevent the expansion or enlargement of the physical structure in the X-ray image caused by reconstruction but it does shift the Hounsfield values of the calcium signal (cross-broken line curve) in the chosen windowing range. As a result a large part of the calcium signal is distributed among different and a plurality of gray scales, and this allows an optical differentiation by a user and results in a clear reduction in calcium blooming. The calcium plaque is accordingly then mapped only in the lightest gray scale in the region of its actual width (−10 to +10).

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. §112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for generating X-ray image data of an examination object, the X-ray image data being calculated from X-ray projection data including one first and at least one second X-ray projection data record acquired with an energy-selective X-ray detector and each acquired in respect of a respective specific energy window, comprising:
   determining a calcium content in the X-ray projection data by way of a base material analysis, the calcium content describing a calcium-determined part of the X-ray attenuation caused by the examination object;
   generating a mixed X-ray projection data record with calcium content suppressed by way of a weighting factor to less than one; and
   reconstructing the X-ray image data from the mixed projection data record by applying a reconstruction algorithm.

2. The method of claim 1, wherein the weighting factor for the calcium content is between 0.25 and 0.75.

3. The method of claim 1, wherein the weighting factor for the calcium content is at least one of specifiable and adjustable by a user.

4. The method of claim 1, wherein the weighting factor for the calcium content is determined in accordance with a desired visual impression of the reconstructed X-ray image data.

5. The method of claim 1, wherein base material analysis and generation of the mixed X-ray projection data record is carried out before filter kernel convolution of the reconstruction algorithm.

6. The method of claim 1, wherein, in addition to calcium, the base material analysis is carried out in respect of at least one of the following materials: iodine and human soft tissue.

7. An X-ray image data processing device for generating X-ray image data of an examination object, the X-ray image data being calculated from X-ray projection data including one first and at least one second X-ray projection data record acquired with an energy-selective X-ray detector and each acquired in respect of a respective specific energy window, the X-ray image data processing device comprising:
   a memory storing computer-readable instructions; and
   one or more processors configured to execute the computer-readable instructions such that the one or more processors are configured to
      determine a calcium content in the X-ray projection data by way of a base material analysis, the calcium content describing a calcium-determined part of the X-ray attenuation caused by the examination object;
      generate a mixed X-ray projection data record with calcium content suppressed by way of a weighting factor to less than one; and
      reconstruct the X-ray image data from the mixed projection data record by applying a reconstruction algorithm.

8. An X-ray image data processing device for generating X-ray image data of an examination object, the X-ray image data being calculated from X-ray projection data including one first and at least one second projection data record acquired with an energy-selective X-ray detector and each acquired in respect of a respective specific energy window, comprising
   a determining unit to determine a calcium content in the X-ray projection data by way of a base material analysis, the calcium content describing the calcium-determined part of the X-ray attenuation caused by the examination object;

a generating unit to generate a mixed X-ray projection data record with calcium content suppressed by way of a weighting factor to less than one; and a reconstruction unit set up to generate X-ray image data from the mixed projection data record by applying a reconstruction algorithm.

9. An X-ray system, comprising:

an energy-selective X-ray detector to acquire one first and at least one second projection data record in respect of specific respective energy windows; and the X-ray image data processing device of claim 7.

10. A non-transitory computer readable medium directly loadable into a memory of an image data record processing device, including program code fragments to carry out the method of claim 1 when executed in the image data processing device.

11. The method of claim 2, wherein the weighting factor for the calcium content is at least one of specifyable and adjustable by a user.

12. The method of claim 2, wherein the weighting factor for the calcium content is determined in accordance with a desired visual impression of the reconstructed X-ray image data.

13. The method of claim 2, wherein base material analysis and generation of the mixed X-ray projection data record is carried out before filter kernel convolution of the reconstruction algorithm.

14. The method of claim 2, wherein, in addition to calcium, the base material analysis is carried out in respect of at least one of the following materials: iodine and human soft tissue.

15. An X-ray system, comprising:

an energy-selective X-ray detector to acquire one first and at least one second projection data record in respect of specific respective energy windows; and the X-ray image data processing device of claim 8.

\* \* \* \* \*